United States Patent [19]
Bartig et al.

[11] Patent Number: 6,129,749
[45] Date of Patent: Oct. 10, 2000

[54] MONORAIL LEFT VENTRICULAR ACCESS LEAD

[75] Inventors: Jeffrey T. Bartig, Maplewood; Randy Peterfeso, St. Paul, both of Minn.

[73] Assignee: Cardiac Pacemakers, Inc., St. Paul, Minn.

[21] Appl. No.: 09/139,454

[22] Filed: Aug. 25, 1998

[51] Int. Cl.[7] .................................................. A61B 5/042
[52] U.S. Cl. ........................... 607/122; 607/125; 600/381
[58] Field of Search ...................................... 607/122, 125, 607/126, 128; 600/585, 381, 374

[56] References Cited

U.S. PATENT DOCUMENTS

| | | | |
|---|---|---|---|
| 5,003,990 | 4/1991 | Osypka | 600/585 |
| 5,304,218 | 4/1994 | Alferness | 607/122 |
| 5,381,790 | 1/1995 | Kanesaka | 607/125 |
| 5,782,760 | 7/1998 | Schaer | 607/122 |
| 5,803,928 | 9/1998 | Tockman et al. | 607/122 |
| 5,895,355 | 4/1999 | Schaer | 607/122 |
| 5,902,331 | 5/1999 | Bonner et al. | 607/122 |

*Primary Examiner*—Carl H. Layno
*Attorney, Agent, or Firm*—Nikolai, Mersereau & Dietz, P.A.

[57] ABSTRACT

A pacing lead for a cardiac stimulator that includes an elongated flexible insulating lead body. An electrode is attached to the lead body at its distal end. An elongated conductor extends through a lumen of the elongated lead body for connecting the electrode to the terminal pin. The conductor is in the form of a coiled wire until it reaches approximate the electrode. It is then crimped to a cable conductor which in turn is crimped or welded to the electrode. The electrode is supported at the distal end by a molded support body which includes a lumen for a guide wire.

6 Claims, 2 Drawing Sheets

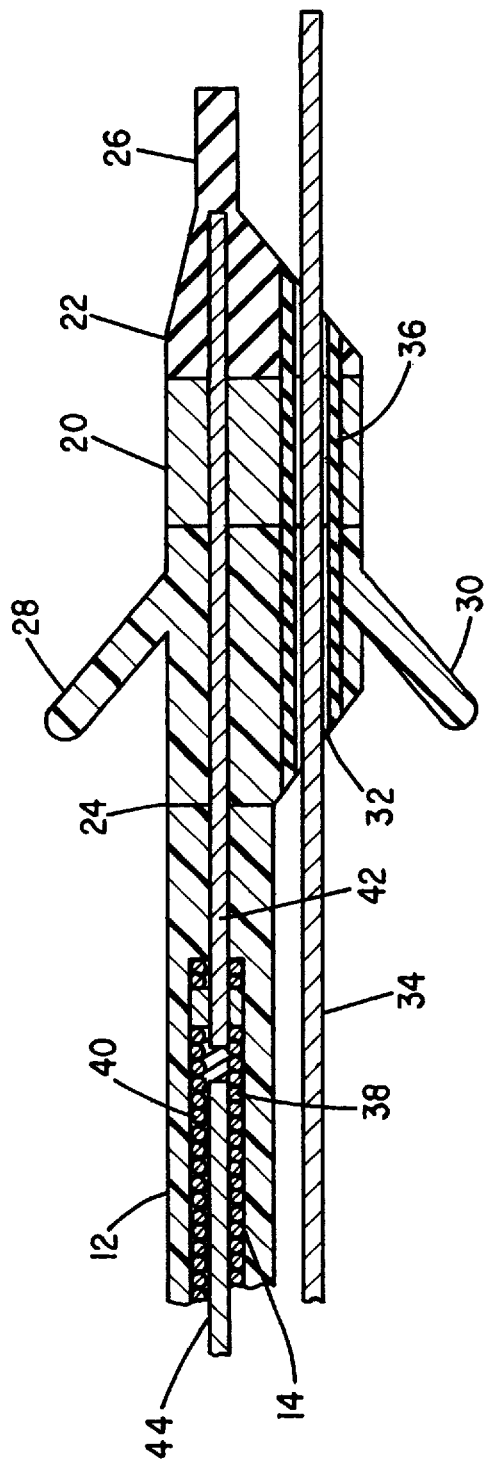
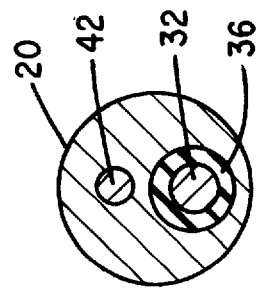

MONORAIL LEFT VENTRICULAR ACCESS LEAD

BACKGROUND OF THE INVENTION

1. Field of the Invention

This invention relates generally to cardiac pacing leads, and more particularly to an apparatus and method for inserting such leads.

2. Discussion of the Prior Art

Cardiac pacemakers for treating bradycardia commonly employ pacing leads for connecting an electrical pulse generator to excitable cardiac tissue, usually within the heart's right ventricle. Such leads have one or more electrodes proximate the distal end thereof and also commonly employ tines located just distal of the tip electrode for holding that electrode in contact with endocardial tissue in the right ventricle. The tines engage the trabeculae, resisting movement of the lead tip due to body movement and/or contractions of the heart muscle itself.

More recently, researchers have found that cardiac stimulation can have a beneficial effect in treating patients suffering from congestive heart failure (CHF). By properly controlling the AV interval of the pacemaker, a sick heart may be made to pump more efficiently. Pacing therapy for the treatment of CHF, however, often requires the ability to stimulate the left ventricle, either alone or in conjunction with right ventricular stimulation. Current methods for achieving left ventricular pacing require placement of an epicardial lead, via thoracotomy or a thoracoscopic approach. Because of the usual poor condition of CHF patients, both of these procedures are "high risk" due to the trauma of the surgery itself and the need for general anesthesia. To obviate the need for a thoracotomy, left ventricular access (LVA) leads have been developed that may be introduced through the coronary sinus and then advanced through the coronary veins so that the lead's stimulating tip electrode can be positioned on the surface of the left ventricle near the apex of the heart.

In co-pending application (Ser. No. 08/788,647), assigned to the same assignee as the present invention, an over the wire lead design is disclosed. This particular application uses a guide catheter and guide wire for placing the lead in the coronary sinus and left sided coronary veins. This over the wire design, as with other conventional over the wire designs, requires that the guide wire pass through an inner lumen of the lead for the entire length of the lead, resulting in considerable drag as the lead is tracked over the wire. While lubricious coatings are used to reduce friction between the leading guide catheter, a significant amount of drag still exists.

Feeding an endocardial or intravenous lead along the desired predetermined path to implant the electrode or electrodes in a desired implantation site, either in a chamber of the heart or in the selected coronary vein, can be sometimes difficult. This is especially true for routing leads through the coronary sinus and into a branching vein on the left myocardium. The difficulties often are a result of anomalies in the vascular anatomy and the number of veins encountered when locating the desired path. Furthermore, the stylet and guide wire has to be rigid enough to afford pushability to the lead and to provide navigation to the lead so as to arrive at the desired location. However, because of the tortious anatomy, a stiff lead may cause damage to the coronary veins.

Therefore, what is needed is a LVA lead that has minimal friction between the lead and guide wire as the lead is positioned and which additionally has a suitable flexible distal section to improve tractability through the tortious anatomy and minimize risk of damage to coronary veins.

OBJECTS OF THE INVENTION

The primary object of the present invention is to provide an implantable lead that minimizes the drag caused by the guide wire as the lead passes over the guide wire during placement of a lead in the coronary veins.

A further object of the present invention is to provide a lead having a more flexible distal end to improve its movement through the tortuous coronary anatomy and minimize risk of damage to the coronary veins during placement of the lead.

Another object of the present invention is to provide a lead that permits use of a guide wire and stylet for positioning the lead with minimal friction developing between the guide wire and the lead.

SUMMARY OF THE INVENTION

The present invention comprises an implantable lead for placement in a selected coronary vein. It includes a lead body with at least one pacing electrode carried on a distal end portion and an elongated conductor coupled to the electrode. The conductor extends through a lumen in the lead body electrically joining a terminal pin at a proximal end of the lead body. The conductor is coiled along most of the length of the lumen. Proximate the electrode, the conductor coil forms a flexible conductor cable which is crimped or welded to the pacing electrode. The pacing electrode is supported on a molded support located at the distal end of the lead. This support includes a lumen for receiving a guide wire therethrough.

DESCRIPTION OF THE DRAWINGS

These and other objects and advantages of the present invention will become readily apparent to those skilled in the art from the review of the following detailed description of the preferred embodiment, especially when considered in conjunction with the accompanying drawings in which like numerals in the several views refer to the corresponding parts:

FIG. 2 is a cross sectional view of the distal end of the lead taken along 2—2 in FIG. 1; and FIG. 3 is a cross sectional view taken along line 3—3 in FIG. 1.

DESCRIPTION OF THE PREFERRED EMBODIMENT

Figure 1:
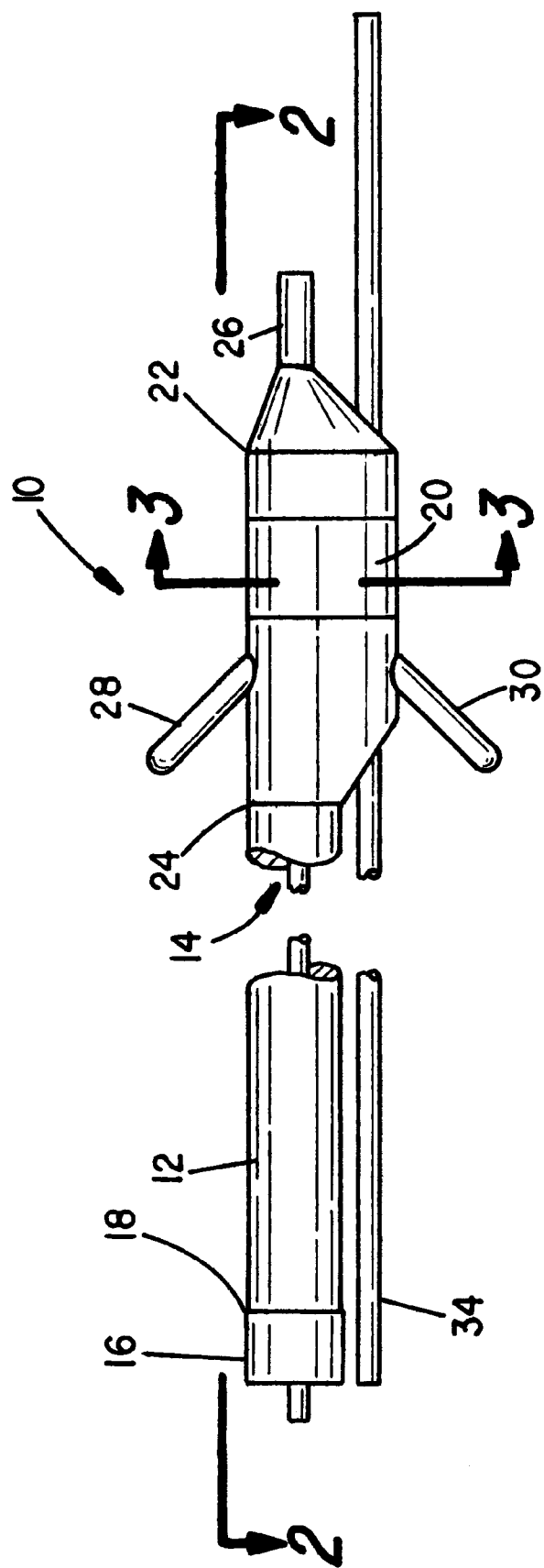
FIG. 1 is a side elevational view of the pacing lead of the present invention.

Referring to FIG. 1, there is indicated generally by numeral 10, a pacing lead specifically designed to be routed through the coronary sinus and into the great cardiac vein or branch vein, transversing the epicardium of the left ventricle. The lead 10 preferably comprises an elongated tubular member 12 with a lumen 14 extending from a terminal pin 16 on its proximal end 18 to an electrode 20 supported on a molded support 22 at its distal end 24. The elongated tubular member 12 is preferably made of a flexible electrically insulative material, such as silicone. The molded support 22 includes an atraumatic tip 26, the electrode 20 and tines 28 and 30 for holding the electrode 20 in contact with the endocardial tissue as is well known to those of skill in the art. The molded support 22 includes a lumen 32 (FIGS. 2 and 3) for receiving a guide wire 34 therethrough. Lumen 32 has an insulative layer 36 separating the lumen 32 from the electrode 20 as seen in FIG. 3 to prevent shorting out to the guide wire during implantation of the electrode 20. Those skilled in the art will recognize that either a ring electrode or a tip electrode are appropriate and suitable for this application. The outer surface of the tubular member 12 is preferably treated to prevent fibrotic attachment and to reduce inflammation response to the lead.

Extending through the lumen 14 of the elongated tubular member 12 is a conductor coil 38. Its distal end 40 is crimped or welded to a conductor cable 42. The conductor cable 42 is preferably titanium and extends through the electrode 20 to which it is crimped or welded. The conductor transition from a coil 40 to a cable 42 provides a very flexible distal section at the lead distal end 24 to assist in navigating the tortuous anatomy of the cardiac veins.

A lumen defined by the helically wound coil 38 is further capable of receiving a removable stylet 44 that will assist in the implantation of the electrode 20 and then be removed once the lead 10 is positioned at the implantation site. The lumen of coil 38 is preferably coated with a lubricious material, such as polytetrafluoroethylene (PTFE), for example, that can coat the lumen to make it easier to insert or remove the stylet 44. While not shown in any of the views, leads of the present invention will have one or more connectors of a type known in the art at its proximal end for mating with the pacer and/or defibrillator pulse generator so depolarization signals originating in the heart can be sensed and stimulating pulses applied in accordance with the device's control algorithms.

The method of implanting the pacing lead 10 involves first routing the guide wire 34 to the desired location. The pacing lead 10 may then be inserted over the guide wire 34 with the guide wire 34 only extending through the lumen 32 located in the molded support 22. This will minimize drag caused by friction as the lead 10 is passed over the guide wire 34 to the selected position. Additionally, the transition of the conductor coil 40 into the conductive cable 42 allows the lead 10 to be readily routed through the tortuous anatomy to the desired position. The stylet 44 may be used in the lumen of the coil 38 if added stiffness is needed. Once the lead 10 is in position, the guide wire 34 and stylet 44 are removed, the tines 28 and 30 assist in anchoring the lead 10 in position until appropriate fibrotic attachment occurs. While two tines are shown, one tine or more than two tines may be used as can be seen by one of skill in the art.

This invention has been described herein and in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without parting from the scope of the invention itself.

What is claimed is:

1. A pacing lead for a cardiac stimulator, said pacing lead comprising:
   a) an elongated flexible insulating lead body having a proximal end, a distal end and a lumen extending therebetween;
   b) an electrode attached to the lead body at its distal end;
   c) coupling means attached to the proximal end for coupling said electrode to said cardiac stimulator;
   d) an elongated, helically wound conductor having a proximal end and distal end, and a flexible conductor cable disposed in the lumen for connecting the electrode to the coupling means, the helically wound conductor defining a removable stylet receiving lumen, the distal end of the helically wound conductor being joined to the flexible conductor cable; and
   e) a guide wire lumen positioned approximate said distal end of said lead body and adapted to receive a guide wire therethrough.

2. A pacing lead of claim 1 wherein said conductor cable is operatively coupled to said electrode.

3. A pacing lead of claim 1 and further including an electrode support at said distal end of said elongated lead body, said electrode support including said guide wire lumen with an insulating layer isolating said electrode from said guide wire extending through the guide wire lumen.

4. A pacing lead of claim 1 wherein said coupling means is a terminal pin.

5. A pacing lead for a cardiac stimulator, said pacing lead comprising:
   a) an elongated flexible insulating lead body having a proximal end, a distal end and a lumen extending therebetween, said lead body dimension to be passed through the great coronary vein;
   b) an electrode attached to the lead body at its distal end;
   c) a terminal pin attached to the lead body at its proximal end;
   d) an elongated spiral wound conductor and a flexible conductor cable disposed in the lumen and connected in series relation for coupling the electrode to the terminal pin, the spiral wound conductor being proximal of the flexible conductor cable and defining a further lumen for receiving a removable stylet therein; and
   e) a guide wire lumen positioned approximate said distal end of said lead body.

6. A pacing lead of claim 5 wherein said conductor cable is operatively coupled to said electrode.

* * * * *